United States Patent [19]

Virgulto et al.

[11] 4,240,444
[45] Dec. 23, 1980

[54] APPARATUS FOR SENSING COUGHS

[76] Inventors: James A. Virgulto, 119 Terrace Ave., West Haven, Conn. 06516; Peter E. Snyder, 11 Hurd Bridge Rd., Clinton, Conn. 06413

[21] Appl. No.: 929,637

[22] Filed: Jul. 31, 1978

[51] Int. Cl.³ .............................................. A61B 5/10
[52] U.S. Cl. ................................... 128/782; 128/721; 128/690; 73/777
[58] Field of Search ............... 128/671, 688, 687, 690, 128/721–722, 630, 650, 689, 773, 780, 782, 774, 716; 73/81, 777

[56] References Cited

U.S. PATENT DOCUMENTS

| | | | |
|---|---|---|---|
| 286,795 | 10/1883 | Edwards | 128/688 |
| 2,194,809 | 3/1940 | Powell, Jr. | 128/721 |
| 2,555,422 | 6/1951 | Scott et al. | 128/689 |
| 2,658,505 | 11/1953 | Sheer | 128/687 |
| 3,154,066 | 10/1964 | Grindheim et al. | 128/687 |
| 3,154,067 | 10/1964 | Stenstrom et al. | 128/687 |
| 3,392,576 | 7/1968 | Hollander, Jr. | 73/777 |
| 3,858,575 | 1/1975 | Rose | 128/773 |
| 3,945,373 | 3/1976 | Tweed et al. | 128/782 |

FOREIGN PATENT DOCUMENTS 1006581  4/1951  Fed. Rep. of Germany ........... 128/687

*Primary Examiner*—Kyle L. Howell
*Attorney, Agent, or Firm*—Jeremiah J. Duggan; Alan H. Spencer

[57] ABSTRACT

A device for sensing the occurrence and magnitude of coughs. The cough sensor is contained within an annular housing having internally mounted sensing means resiliently biased to axially extend beyond the housing. Electrical actuation of circuit means by longitudinal movement of the sensing means generates signals. The device is secured to a predetermined location on the patient's body by a belt suitably attached thereto or other appropriate means capable of retaining the device in close proximity to a body muscle involved in the production of coughs.

13 Claims, 5 Drawing Figures

APPARATUS FOR SENSING COUGHS

BACKGROUND OF THE INVENTION

This invention generally relates to the field of electromechanical sensing devices and more particularly to a device and method for sensing coughs emanating from the human body.

In recent years increased concern with consumer interest and corresponding governmental activity principally promulgated in the rules and regulations of the Food and Drug Administration and the Federal Trade Commission have made it desirable, if not mandatory, for suppliers of products, particularly those relating to or having affect on body function, to determine efficacy. One group of products undergoing close scrutiny are those preparations intended for the amelioration or decrease in frequency of the human cough. In conducting tests and studies in this area it immediately became evident to researchers that no accurate, dependable, and relatively portable device existed for sensing coughs.

Prior art devices while inherently capable of sensing and measuring coughs have proven incapable of discerning coughs from those other body functions which produce similar body manifestations. In sensing human coughs it is necessary that the device be able to determine or distinguish normal breathing and body movement therefrom.

A number of prior art patents which deal generally with the sensing and determination of body functions are: U.S. Pat. Nos. 1,619,005; 3,154,066; 3,727,606; 3,760,794; 3,782,368. All fail in one mode or other to either teach or suggest a body function monitor capable of sensing and recording human coughs with sufficient accuracy to permit use in tests of product efficacy. The most pertinent of these prior art patents is considered to be Pat. No. 3,154,066 entitled "Body Function Sensors" issued to Grindheim et al. on Oct. 27, 1964.

The instrument of this patent utilizes mechanical movement of a sensing member to alter the electrical characteristics of a strain gauge and thereby produce an electrical signal corresponding to the body function in question. The patent teaches the use of this device for the measurement of breathing and pulse rates. While in some limited mechanical details the device is similar to that of the present invention it has certain requisites that not only make it inapplicable to the sensing of coughs but inherently render it incapable thereof. In operation it is required that the device of this prior art patent be in some fashion or other snugly although not too tightly secured to the body in such a manner that the housing of the device is rendered substantially immovable by resting on skeletal structure of the body. This arrangement prevents the device from distinguishing body contortions or the act of breathing from a human cough, since both of these body functions as well as most others produce relative movement of tissue with respect to the skeletal frame.

To overcome problems associated with the prior art and to permit testing of product efficacy, it is the object of the present invention to provide a new and improved cough sensing device. It is a further object of the present invention to produce a cough sensor relatively insensitive to other body functions. It is another object of the present invention to produce a reliable and economical cough sensing device. It is yet another object of the invention to produce a cough sensor capable of transmitting signals to remotely located recording equipment. It is still another object of the present invention to provide a cough sensor capable of being comfortably carried and worn by the patient for extended periods.

SUMMARY OF THE INVENTION

In meeting the foregoing objects and in overcoming prior art problems the present invention contemplates a cough sensor contained in a housing which is secured to a predetermined location on the body of a patient by suitable attachment means. Within the housing there is mounted sensing means which is resiliently biased to longitudinally extend beyond the housing and in contact with the body. Also operatively associated with both the housing and the sensing means is means capable of generating signals relative to the longitudinal movement of the sensing means with respect to the housing in response to the human cough.

Another aspect of the invention contemplates a cough sensor in which the housing makes contact with the body of the patient by means of an annular axially extending wall member formed along its base. The sensing means mounted to the housing comprises a radially extending disc member having an axial shaft which is slidably mounted to and biased to extend beyond the housing by a spring member. The distal end of the shaft is operatively associated with signal generating means for producing an output signal proportional to axial movement of the shaft in response to a cough.

In another aspect, the present invention contemplates a method for detecting and measuring coughs. A cough sensing device having an annular base wall member from which axially extends a resiliently biased sensing member is brought into snug contact with an area of the body in which is located muscle tissue associated with the production of coughs. Upon tensing of the muscle, for example the rectus abdominis muscle of the stomach, the protruding sensing means is caused to move axially with respect to the annular housing. Movement of the sensing means causes means operatively associated with the housing and the sensing means to generate signals relative to such movement, which signals are indicative of the cough and its magnitude.

Other objects and aspects of the invention will become clear on consideration of the detailed description of the invention in conjunction with the following drawings.

DESCRIPTION OF A PREFERRED EMBODIMENT

The frequency duration and relative force of coughs may be measured by denoting the changes in certain muscles of the body which act in their production. Although a number of different muscles may find application with a device made in accordance with the preferred embodiment of this invention, the rectus abdominis muscle of the stomach offers advantages.

Anterolateral abdominal wall muscles, principally the rectus abdominis, have a number of functions, among these being: (1) protection of underlying viscera; (2) expelling substances from the body by incresing interabdominal pressure and compressing the abdominal wall, and (3) in bending the body forward or flexing the vertebral column. In performing all these functions the rectus abdominis muscle tenses and brings about the required increase in interabdominal pressure and contraction of the abdominal wall.

The rectus abdominis muscle is a long straplike muscle that arises from the pubic bone and its ligaments. It widens as it extends upward to insertion on the anterior surface of the Zyphoid process and the costal cartilages of the fifth, sixth and seventh ribs. It is entirely enclosed in the sheath formed by the apaneuroses of the muscle of the lateral wall of the abdomen. These muscles are antagonists of the diaphragm, relaxing as the diaphragm contracts and contracting as it relaxes. A device capable of sensing the tensioning of this large powerful muscle may therefore be used to not only determine coughs but also the functions of vomiting, defecation, childbirth and sneezing.

In determining the efficacy of pharmaceutical products in reducing the bodily cough function or merely the frequency of cough in an individual, the device of the present invention placed in contact with this muscle provides satisfactory measurements and indications of cough. Some of the other functions associated with movement of the rectus abdominis muscle may however give false readings of coughs but in actual practice these may be easily avoided and recognized. It is assumed that subjects undergoing tests will not be used who are either vomiting or undergoing childbirth, and defecation is an infrequent occurrence which can be taken into account. Sneezing may cause readings similar to a cough but it is possible to deal with this unless the subject is having a bout of frequent sneezing. One method for determining the presence of sneezing is to have a sound recording made while the patient is undergoing scrutiny or by increased analytical review of the recorded information. Heavy lifting and strenuous exercises in which the rectus abdominis muscle plays a part may be eliminated during the study and hence are not considered to constitute a problem.

Figure 1:
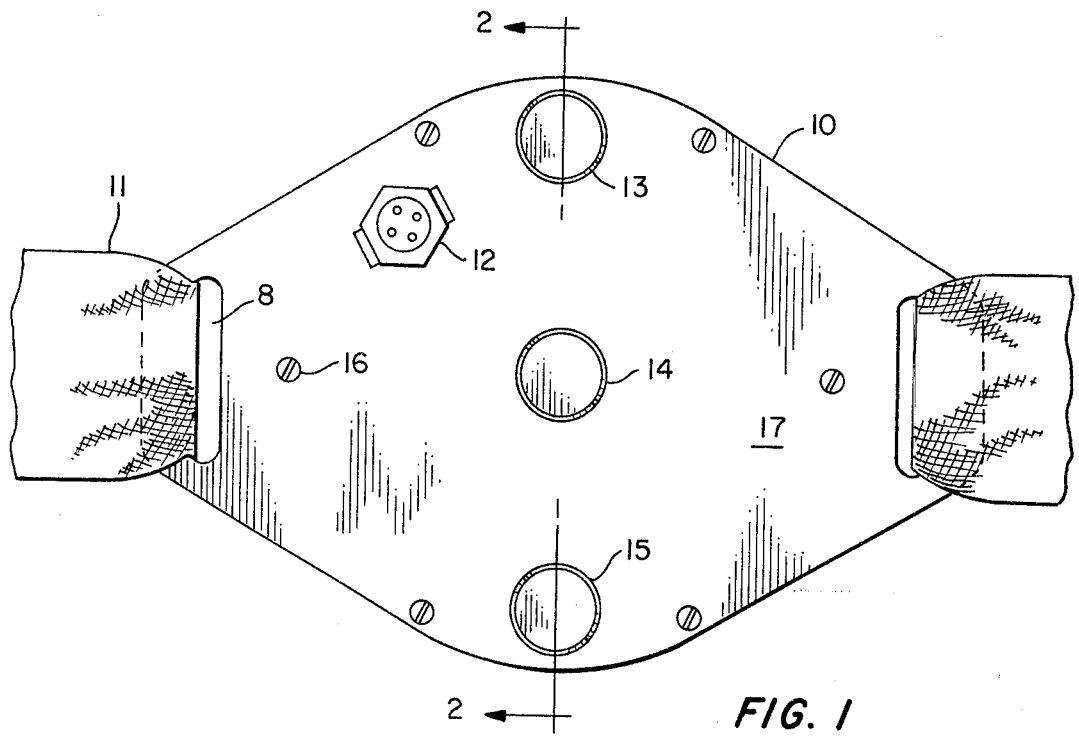
FIG. 1 is an outline plan view of the cough sensor as mounted to the body of the patient.
Figure 2:
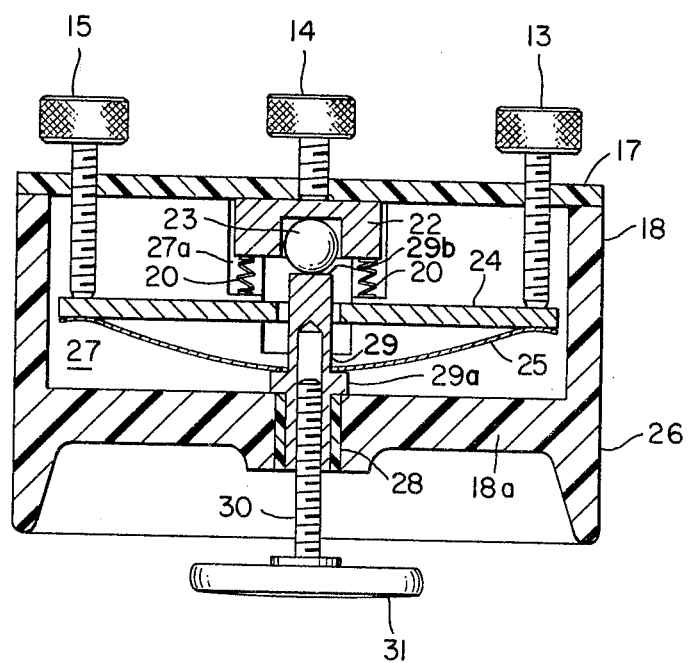
FIG. 2 is a cross sectional view of the cough sensor of FIG. 1.

Considering FIGS. 1 and 2 together, the cough sensor of the present invention is shown and disclosed in sufficient detail for a full understanding of the invention. FIG. 1 is a plan view showing an annular type unit in the position the device would assume when secured to the patient undergoing study. Annular housing 10 principally comprises two components or members, a cover member 17 enclosing an annular partially open chamber member 18, terminating in an annular wall base member 26, which is placed in actual contact with the skin of the patient. Cover member 17 is secured to chamber member 18 by means of six longitudinally extending screws 16. It must of course be recognized that any suitable means for fixing cover 17 to chamber 18 may be utilized within the context of this invention. On either terminal end of cover 17 a flange is formed to which is attached a belt or body fastening means. Belt 11 is fastened to cover 17 by welding or soldering of belt termination member 8 thereto but may be affixed to cover 17 in any manner such as by riveting, cementing, etc., as long as it has sufficient integrity to retain cough sensor 10 in place on the body. Once cough sensor 10 is placed in the proper or predetermined location on the patient, belt 11 is placed around the body and snugly secured thereto by appropriate coupling means such as a buckle arrangement or multiple complementary hook and eye fibers on opposite ends thereof respectively (Velcro ® fasteners).

Annular chamber 18 is used to enclose both the mechanical, fluid and electrical members of the cough sensing unit. The sensing means of this device comprises a radially extending disc member 31 which is axially located of annular chamber 18 and longitudinally extends beyond annular base 26. The extension of disc 31 beyond base 26 is a matter of selection in determining overall device response and comfort for the patient undergoing study. It must be realized that the magnitude of signal generated varies from patient to patient and hence while the unit may be calibrated for normal sensitivity it is usually necessary to alter such calibration for each individual undergoing study. Disc 31 normally has a diameter of approximately 1.25 inches and its base has a shallow convex curvature with a smooth margin. In order to keep the moment of inertia of the sensing means as low as possible, disc 31 is fabricated from any suitable plastic material but may also be fabricated from metal without seriously affecting the operational capability of the device.

Axially extending from disc 31 is threaded member or shaft 30. Shaft 30 is threaded internally of concentric collar member 29. Shaft 30, in the preferred embodiment, is a 3/16 aluminum diameter rod with an 8/32 thread, but any suitable combination of rod and thread may be used as long as it permits sufficiently fine adjustablility of shaft 30 with respect to insertion in collar 29. Collar 29 extends through base wall member 18a of annular housing 18 and is guided therethrough by a vertical axial bearing 28 or other suitable bushing. It has been found that a teflon type bushing is sufficient for both purposes of axial guidance and radial restraint while offering minimal friction to movement of collar 29 through base wall member 18a. Collar 29 has located thereon an annular flange 29a one shoulder of which rests upon the upper surface of wall 18a thereby restricting further longitudinal extension, and the opposite shoulder bears against leaf spring member 25.

Leaf spring 25 is fabricated of spring steel but may be made from any suitable spring material such as berylium copper. It is located by an constrained within a slot 27 formed in annular housing 18 and has a substantially rectangular shape with a centrally located aperture through which the cylindrical distal terminus of collar 29 may pass but not the shoulder of the annular flange member 29a. The tension or spring force of leaf spring 25 may be adjusted and calibrated by movement of bearing plate 24 which contacts spring member 25 at its terminal extremes. Plate 24 is constrained within the same cavity 27 and has substantially the same rectangular dimensions as spring member 25. Bearing plate 24 has a centrally located aperture therein through which collar member 29 may pass. The axial longitudinal movement of plate 24 is controlled and adjusted by calibration screw members 13 and 15 longitudinally extending through cover 17 and bearing against the upper surface of plate 24 at its extreme terminal ends.

Calibration screw members 13 and 15 are approximately 1″ in length having a 10/32 thread thereon and mate with internally threaded complementary apertures in cover 17. For ease of adjustment each of calibration screws 13 and 15 are provided with an approximately ⅛" diameter knurled knob to permit gripping and easy turning. As these members are turned clockwise the threaded portions extend further into chamber 18 bearing against plate 24 and thereby causing increased tension in spring 25 with commensurate or corresponding increased resistance to longitudinal movement of collar 29. When disc 31 located at the proximal terminal end of the sensing means is displaced by the muscle, the distal end thereof formed by collar 29b comes into contact with signal generating means which ultimately produce an electrical signal corresponding to such movement in response to patient coughs.

Distal end 29b of collar member 29 contacts a fluid or as in this case an air filled resilient bulb 23, which is sealed to the atmosphere. As collar 29 moves in response to deflection of disc 31 it causes bulb 23 constructed of neoprene rubber or other flexible material, to compress thereby generating an increase in pressure with respect to atmospheric. This increased internal pressure is sensed by electrical components and circuitry producing a desired signal responsive to axial movement of the sensing means.

Flexible chamber or bulb 23 is contained within a second slot 27a formed in housing 18. Bulb 23 is constrained between the distal end 29b and a slot formed in a holding member 22, the slot having a lateral dimension corresponding to that of bulb 23. As collar 29 moves longitudinally it compresses the bulb 23 against the base of the slot in holding member 22 and induces a change in internal pressure. Initial calibration of the pressure signal output is permitted by longitudinal movement of holding member 22 within complementary slot 27a of chamber 18.

Holding member 22 of substantially rectangular shape is supported on its four corners by axial helical springs 20. Bearing against the top of hold member 22 is a calibration screw 14 similar in construction to calibration screws 13 and 15 as heretofore described. Axial extension or retardation of calibration screw 14 either further compresses or relaxes bulb 23 during initial calibration and placement of the unit on the patient undergoing study.

Figure 3:
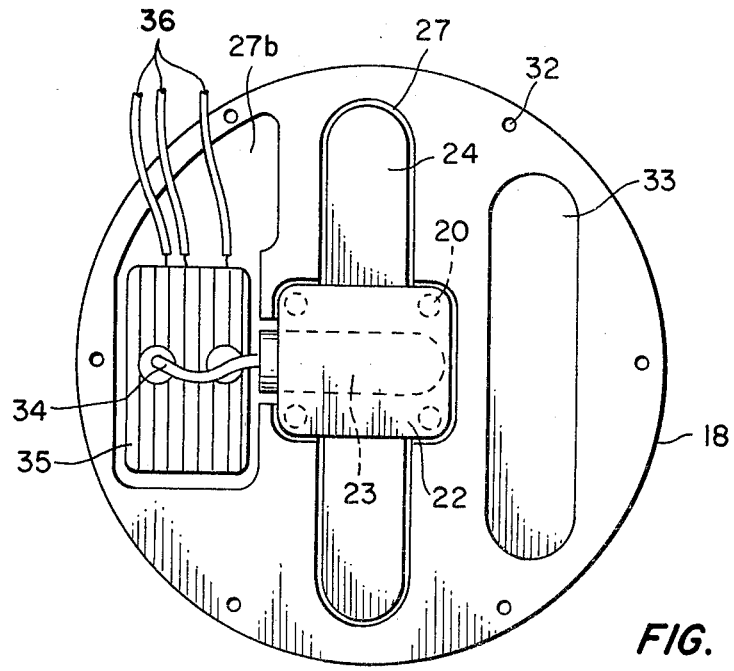
FIG. 3 is a plan view of the cough sensor of FIG. 1 with a top cover member removed.

Referring to FIG. 3 the cough sensing device is shown with top cover 17 removed. Clearly discernible in this view are slots 27 and 27a formed in chamber 18 to hold and constrain bearing plate 24 and holding member 22 respectively. Also visible is a second slot 27b intended to hold and house strain gauge 35 which is connected to the output of bulb 23 through line or tube 34. Electrical leads 36 are provided for necessary circuit connections and to convey power to ancillary unit 35. Internally threaded holes 32 are provided for threadable engagement with cover 17 holding screws 16 and slot 33 in housing chamber 18 is for lightening purposes. Ancillary unit 35 is a silicon strain gauge Model LX1600 or 1700 Differential Transducer Series produced and marketed by National Semiconductor Corporation or equivalent, well known to those of ordinary skill in the art. Internal pressure of bulb 23 is communicated to strain gauge 35 by line 34 to one side of an internal diaphragm, the other side of which is exposed to atmospheric, thereby producing a differential pressure corresponding to the change in internal pressure of bulb 23. Strain gauge 35 forms a part of a bridge circuit located in instrumentation remote from the unit. Electrical connections are made through lines 36 interconnected with external equipment by means of female plug unit 12 located on cover 17.

As pressure in bulb 23 is altered in conformance with axial movement of collar 29, resistance i.e. electrical resistance, of strain gauge 35 is altered thereby producing an electrical output signal from the external bridge circuitry proportional to axial movement of the sensing means as induced by tensioning of the rectus abdominis or other selected body muscle.

Figure 4:
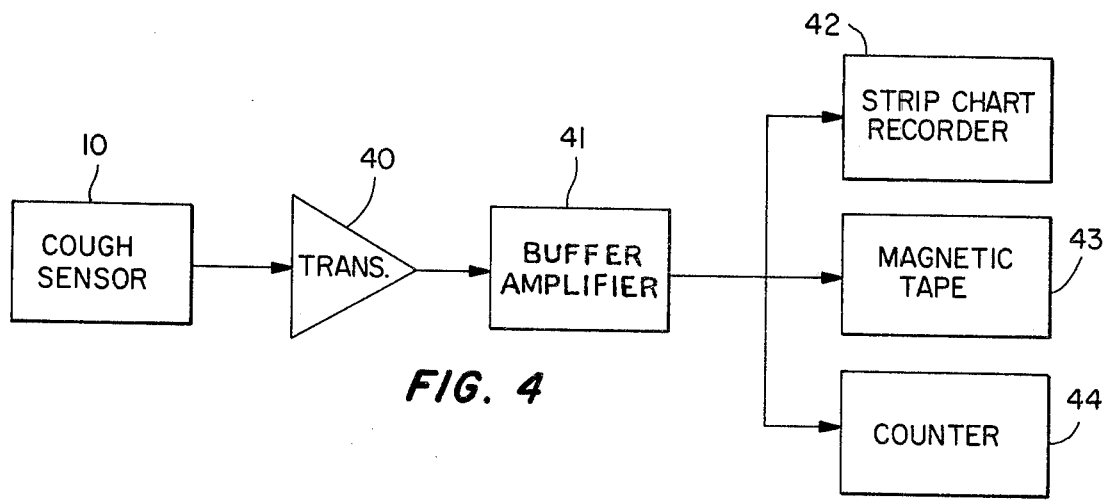
FIG. 4 is a schematic block diagrammatic presentation of the signal generating and recording portions of the cough sensing unit.

Referring to FIG. 4 the cough sensor unit 10 is shown as connected through suitable cabling to a transmitter unit 40 which contains the necessary external bridge circuitry. The output signal is communicated to buffer amplifier unit 41, the output of which is used to drive any desired number of external indicators for example strip chart recorder 42, audio tape unit 43, and/or counter 44. The output signal may also be communicated to remotely located recording and measuring equipment by selected radio transmitting equipment carried by the patient and associated with the cough sensor.

Figure 5:
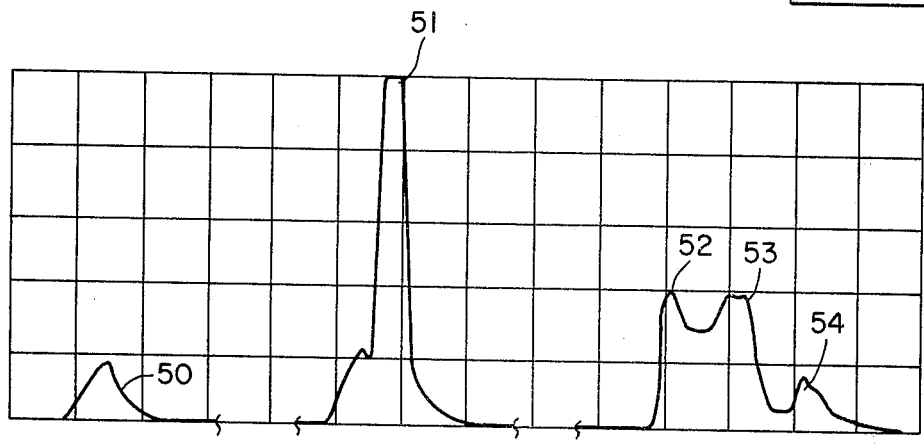
FIG. 5 is a schematic representation of typical signals generated by the apparatus of FIG. 4.

In FIG. 5 is shown in schematic outline a schematic chart recording of the output of the cough sensor of this invention. Pulse outlines 50, 52, 53 and 54 may be those typically associated with body functions other than coughs. Waveform 51 ideally demonstrates the degree of discernment which is possible between a cough and other body functions. To further minimize any ambiguity in cough signal determination, it has been found advantageous to employ differentiation circuitry with this preferred embodiment of the invention.

When using differentiation, the output signal generated by cough sensor 10 is conducted to a first derivative circuit means, the output of which drives a second buffer amplifier (which may be contained within buffer amplifier 41). The second buffer amplifier output is then used to drive recording devices. Under normal operating conditions, it has been found that a range of time constants of approximately 10 to 100 milliseconds present acceptable differentiation performance.

The use of differentiation allows a clearer distinction between cough generated signals and those having other than cough origin. Given a properly selected time constant the artifact signals produced by other than coughs may be virtually eliminated. It is emphasized however that although differentiation enhances interpretation of output signals, it is not necessary to the accurate performance of the unit. In actual practice, it has been found that the device of this invention produces and measures cough indications with a degree of accuracy and precision in excess of 98%.

To better understand this invention and to appreciate its novel characteristics, a typical operational performance of the unit in a patient study is considered. The cough sensor is placed on the person of the patient located in the upper right quadrant of the abdomen below the rib cage, assuming the rectus abdominis muscle is to be used. The unit is snugly but not too tightly stapped to the patient so that annular wall member 26 depresses the muscle as to assure operational reliability of the equipment but not produce patient discomfort. With the patient in a quiescent state the axial location of shaft 30 with respect to annular base member 26 is adjusted in conjunction with bulb 23 adjustment screw 14 until no discernible output from the device is obtained. Then with patient induced coughing, adjustment screws 13 and 15 are axially altered in order to produce output signals of desired magnitude and within the scale requirements of the external recording and monitoring equipment. Upon accomplishment of this, the patient or individual undergoing study, may then be allowed to assume normal but limited activities.

When the cough sensor is subjected to a cough spasm either naturally occurring or induced for calibration purposes, the rectus abdominis muscle, upon which the annular base member 26 is located, is tensioned causing an upward axial movement of disc 31, shaft 30 and collar 29. This movement causes deformation of bulb 23 resulting in increased internal pressure which is communicated and sensed and measured by the effect on strain gauge 35. Strain gauge 35 in combination with remote external circuitry connected through conductors 36 produces the desired electrical output signal proportional to the magnitude of the induced or naturally occurring cough.

Thus the sensor of this invention is capable of producing a signal indicative of the nature and magnitude of the body function in question without the necessity of being placed on or constrained by skeletal formation of the body. It produces with a minimum ambiguity, signals indicative of coughs as opposed to other body functions and it accomplishes this by a relative motion of the sensor means formed by disc 31, shaft 30, collar member 29 with respect to the housing 18. It achieves this task with a high degree of accuracy and reliability not found in prior art equipment and has under study conditions been found adaptable and suitable for testing and measuring of the efficacy of pharmaceutical products for the amelioration of coughs. It is the recognition of the function of the appropriate muscles in the generation of body coughs and the electrical, mechanical and fluid members and their arrangement necessary to the sensing and measuring of this muscle action which is neither taught nor suggested in the prior art of record. Therefore, all those modifications which are obvious to one of ordinary skill of the art are considered to be within the ambit and scope of this invention and that the invention is not limited to the illustrated forms of the preferred embodiment.

We claim:

1. A cough sensor comprising:
   an annular axially extending housing;
   sensing means mounted to the housing including a shaft member extending axially of the housing with a radially extending disc member on its proximal end, a concentric collar connected to the shaft and forming a distal end thereof, a leaf spring member interposed between the housing and the shaft member to resiliently urge the disc beyond the housing having a centrally located aperture through which a portion of the concentric annular collar member passes, a flange member connected to the collar member having a first shoulder bearing against the leaf spring in juxtaposition to the aperture and a second opposed shoulder, and a stop member on the housing bearing against the second shoulder for limiting axial extension of the disc beyond the housing;
   means operatively associated with the housing and the sensing means to generate signals relative to movement of the shaft with respect to the housing; and
   attachment means connected to the housing for securing the cough sensor in a predetermined location and attitude on the body so that the annular housing is in contact with and the disc member axially extends toward the body.

2. The cough sensor of claim 1 wherein the collar member slidably engages the housing through a bearing member interposed between the collar member and the housing.

3. The cough sensor of claim 1 wherein the means for generating signals relative to axial movement of the sensing means includes circuit means producing an electrical signal proportional to the axial movement of the collar member.

4. The cough sensor of claim 3 wherein the electrical circuit means comprises a silicon strain gage member electrically connected to external signal generating apparatus.

5. The cough sensor of claim 4 wherein the external apparatus includes signal amplifier means and recording means.

6. The cough sensor of claim 3 wherein a distal end of the portion of the collar member contacts the signal generator means for producing the signals proportional to the axial movement of the disc member.

7. The cough sensor of claim 6 wherein the signal generator means includes a fluid filled sealed member fluidly communicating with a differential pressure sensor and wherein the fluid filled member is compressed upon axial movement of the distal end of the collar member.

8. The cough sensor of claim 7 wherein the fluid filled member is an air filled bulb constrained within a cavity of the housing and located internally of a slot formed in a retaining block resiliently mounted to the housing.

9. The cough sensor of claim 8 wherein the retaining block is a substantially rectangular member mounted on four axial helical springs and is axially movable by an axially extending screw member threadably engaged to the housing.

10. The cough sensor of claim 8 wherein the bulb member fluidly communicates with a silicon strain gage member, and wherein the strain gage in response to increased internal pressure of the bulb member produces an altered electrical characteristic which characteristic is electrically transmitted to external circuit means.

11. The cough sensor of claim 1 wherein the spring tension is controlled by spring calibration means.

12. The cough sensor of claim 11 wherein spring tension is controlled by two adjusting screws mounted to the housing and bearing against terminal ends of the leaf spring respectively and wherein axial adjustment of the screws causes spring tension to be increased or retarded.

13. The cough sensor of claim 12 wherein a bearing plate member is interposed between the leaf spring and the calibration adjust screws and wherein the bearing plate has a centrally located aperture through which the portion of the concentric annular collar member passes.

* * * * *